US00PP18244P2

(12) United States Plant Patent
Van Zanten

(10) Patent No.: US PP18,244 P2
(45) Date of Patent: Nov. 20, 2007

(54) ***OSTEOSPERMUM* PLANT NAMED 'GG DEL WY06'**

(50) Latin Name: *Osteospermum ecklonis*
Varietal Denomination: GG DEL WY06

(75) Inventor: Leo Van Zanten, Oxnard, CA (US)

(73) Assignee: G & G Breeding Corporation, Oxnard, CA (US)

( * ) Notice: Subject to any disclaimer, the term of this patent is extended or adjusted under 35 U.S.C. 154(b) by 0 days.

(21) Appl. No.: 11/394,713

(22) Filed: Mar. 31, 2006

(51) Int. Cl.
*A01H 5/00* (2006.01)

(52) U.S. Cl. ..... Plt./360
(58) Field of Classification Search ..... Plt./360
See application file for complete search history.

*Primary Examiner*—Wendy C. Haas
*Assistant Examiner*—Georgia Helmer

(57) ABSTRACT

A new and distinct *Osteospermum* plant cultivar is disclosed, characterized by medium size daisy type inflorescences, freely flowering under outdoor growing conditions with continuous blooming from spring through autumn, creamy white ray florets, and gray-orange disc florets with a gray-green center.

1 Drawing Sheet

Latin name of the genus and species: *Osteospermum ecklonis.*
Variety denomination: 'GG DEL WY06'.

BACKGROUND OF THE INVENTION

The new cultivar 'GG DEL WY06' is a product of open pollination in a heterogeneous population of *Osteospermum* mass selection. The new cultivar was discovered and selected by Leo Van Zanten in May 2004 in Carpinteria, Calif.

Asexual reproduction of the new cultivar 'GG DEL WY06' by cuttings from adventitious shoots was performed in Oxnard, Calif., and has shown that the unique features of this new cultivar are stable and reproduced true to type on successive generations.

SUMMARY OF THE INVENTION

The cultivar 'GG DEL WY06' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG DEL WY06.' These characteristics in combination distinguish 'GG DEL WY06' as a new and distinct *Osteospermum* cultivar.

1. Daisy type inflorescence;
2. Creamy white ray florets;
3. Gray-orange disc florets with a gray-green center; and
4. A free branching habit.

There is not parent variety to compare to 'GG DEL WY06.'

In comparison to the commercially available variety 'Vanilla Cream' (U.S. Plant Pat. No. 12,149), 'GG DEL WY06' is shorter but wider than the comparable variety. Also, 'GG DEL WY06' has more leaves per lateral branch and obovate-shaped leaves compared to the elliptical leaves of 'Vanilla Cream.' Additionally, the new variety has a smaller inflorescence diameter but a longer inflorescence depth. Also, the upper surface of the ray florets of the new variety 'GG DEL WY06' are more yellow-white than the ray florets of 'Vanilla Cream'. Further, the longitudinal stripes on the lower surface of the ray florets of 'GG DEL WY06' are a lighter, creamier yellow. Finally, the disc florets of 'GG DEL WY06' are gray-orange and gray-green compared to the single gray-green disc florets of the comparable variety.

BRIEF DESCRIPTION OF THE PHOTOGRAPH

The accompanying photograph in drawing illustrates in full color a typical plant of 'GG DEL WY06' grown in a 6-inch pot, planted late October and grown outdoors. The plant is 18 weeks old. The growing temperature ranged from 12° C. to 15° C. at night to 12° C. to 20° C. during the day. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GG DEL WY06' plants grown in Oxnard, Ventura County, Calif., during the months of October through February. The growing temperature ranged from 12° C. to 15° C. at night to 12° C. to 20° C. during the day. Measurements and numerical values represent averages of typical flowering types.

Botanical classification: *Osteospermum ecklonis* cultivar 'GG DEL WY06.'
Commercial classification: Garden-type *Osteospermum.*

PROPAGATION

Time to Rooting: 10 to 14 days at approximately 21° C.
Root Description: Fine, fibrous.

PLANT

Growth Habit: Mounding outwardly spreading herbaceous perennial.
Height: Approximately 27 cm.
Plant Spread: Approximately 45 cm.

Growth Rate: Vigorous.
Branching Characteristics: Free Branching.
Length of Lateral Branches: Approximately 15 cm.
Number of Leaves per Lateral Branch: Approximately 42.
Age of Plant Described: Approximately 130 days.

FOLIAGE

Leaf:
*Arrangement.*—Alternate single.
*Average length.*—Approximately 3.7 cm.
*Average width.*—Approximately 2.1 cm.
*Shape of blade.*—Obovate.
*Apex.*—Abruptly acuminate.
*Base.*—Attenuate.
*Attachment.*—Stalked.
*Margin.*—Entire with occasional tiny serrations.
*Texture of top surface.*—Lightly pubescent.
*Texture of bottom surface.*—Lightly pubescent.
*Leaf internode length.*—Approximately 1.5 cm.
*Color.*—Young foliage upper side: Near Green 137A. Young foliage under side: Near Green 137A. Mature foliage upper side: Near Green 137A. Mature foliage under side: Near Green 137B.
*Venation.*—Type: Pinnate. Venation color upper side: Near Yellow-Green 145B. Venation color under side: Near Yellow-Green 145B.

Petiole:
*Average length.*—Approximately 1.3 cm.
*Color.*—Near Yellow-Green 145B.
*Diameter.*—Approximately 0.2 cm.

BLOOM

Inflorescence:
*Flowering habit.*—Freely flowering under outdoor growing conditions with continuous blooming from spring through autumn and year round in a greenhouse environment.
*Inflorescence form.*—Daisy.
*Natural flowering season.*—Continuous throughout February to September in temperature regions.
*Number of inflorescences per lateral branch.*—Approximately 4 open inflorescences.
*Inflorescence diameter.*—Approximately 4.5 cm.
*Inflorescence depth.*—Approximately 2.6 cm.
*Disc diameter.*—Approximately 1.3 cm.
*Inflorescence longevity on plant.*—Approximately 5 to 10 days; longevity of individual flowers are very dependent on temperature and light conditions.
*Persistence.*—Persistent.

Ray Florets:
*Appearance.*—Matte.
*Texture.*—Smooth.
*Average number of ray florets per inflorescence.*—21.
*Shape.*—Oblanceolate.
*Aspect.*—Slightly cupped, facing upward or outward.
*Margin.*—Entire.
*Apex.*—Obtuse.
*Length.*—Approximately 3.1 cm.
*Width.*—Approximately 1 cm.
*Color.*—Upper surface at first opening: Near Yellow-White 158D. Upper surface at maturity: Near Yellow-White 158D. Upper surface at fading: Near Yellow-White 158D. Under surface at first opening: Near Yellow-White 158D with longitudinal stripes of Yellow 11C to Yellow 11B at apex. Under surface at maturity: New Yellow-White 158D with longitudinal stripes of Yellow 11C to Yellow 11B at apex and Yellow 11A at extreme tip. Under surface at fading: Near Yellow-White 158D with longitudinal stripes of Yellow 11C to Yellow 11B at apex and Yellow 11A at extreme tip.

Disc Florets:
*Appearance.*—Matte.
*Texture.*—Smooth.
*Average number of florets per disc.*—Approximately 90.
*Shape.*—Tubular.
*Apex.*—Five-pointed.
*Average length.*—Approximately 0.4 cm.
*Average width.*—Approximately 0.1 cm.
*Color.*—At first opening: near Greyed-Yellow 160D at very center with near Greyed-Orange 165A at side. At maturity: Near Greyed-Yellow 160D at very center with near Greyed-Orange 165A at side. At fading: Near Greyed-Yellow 160D at very center with near Greyed-Orange 165A at side.

Peduncle:
*Length.*—Approximately 11.2 cm.
*Angle.*—Terminal peduncles, erect; secondary and tertiary peduncles, about 45° From vertical.
*Strength.*—Moderate.
*Color.*—Near Yellow-Green 144A.
*Habit.*—Upright.
*Diameter.*—Approximately 0.1 cm.
*Surface texture.*—Lightly pubescent.

Inflorescence Bud:
*Length.*—Approximately 2.3 cm.
*Diameter.*—Approximately 0.5 cm.
*Form.*—Elliptic.
*Color.*—Near Green-Yellow 1C.

Involucral Bracts (Phyllaries):
*Appearance.*—Matte.
*Texture.*—Lightly pubescent.
*Number.*—Approximately 19.
*Shape.*—Lanceolate.
*Margin.*—Entire.
*Apex.*—Narrowly acute.
*Length.*—Approximately 1.1 cm.
*Width.*—Approximately 0.1 cm.
*Color.*—Upper side: Near Green 137C. Under side: Near Green 137C.

REPRODUCTIVE ORGANS

*Androecium.*—Present on disc florets only. Number of stamens: 5. Anther shape: Linear. Anther length: Approximately 1.2 mm. Anther color: Near Greyed-Orange 165A. Amount of pollen: Minimal. Pollen color: Near Yellow-Orange 20A.
*Gynoecium.*—Present on ray and disc florets. Pistil Number: One. Pistil length: Approximately 4 mm. Stigma shape: Two parted. Stigma length: Approximately 1.1 mm. Stigma color: Near Greyed-Yellow 162B. Style length: Approximately 0.1 cm. Style color: Near Yellow-White 158C.

OTHER CHARACTERISTICS

Disease Resistance: Neither resistance nor susceptibility to diseases or pests has been observed in this variety.
Drought Tolerance/Cold Tolerance: Plants are moderately drought tolerant. Plants need cold, less than 12.8° C. for flower induction.
Fruit/Seed Production: Commercially, this plant is not used or observed in a stage where seeds would be produced. Therefore, seed production has not been observed.

What is claimed is:

1. A new and distinct cultivar of *Osteospermum* plant named 'GG DEL WY06' as herein illustrated and described.

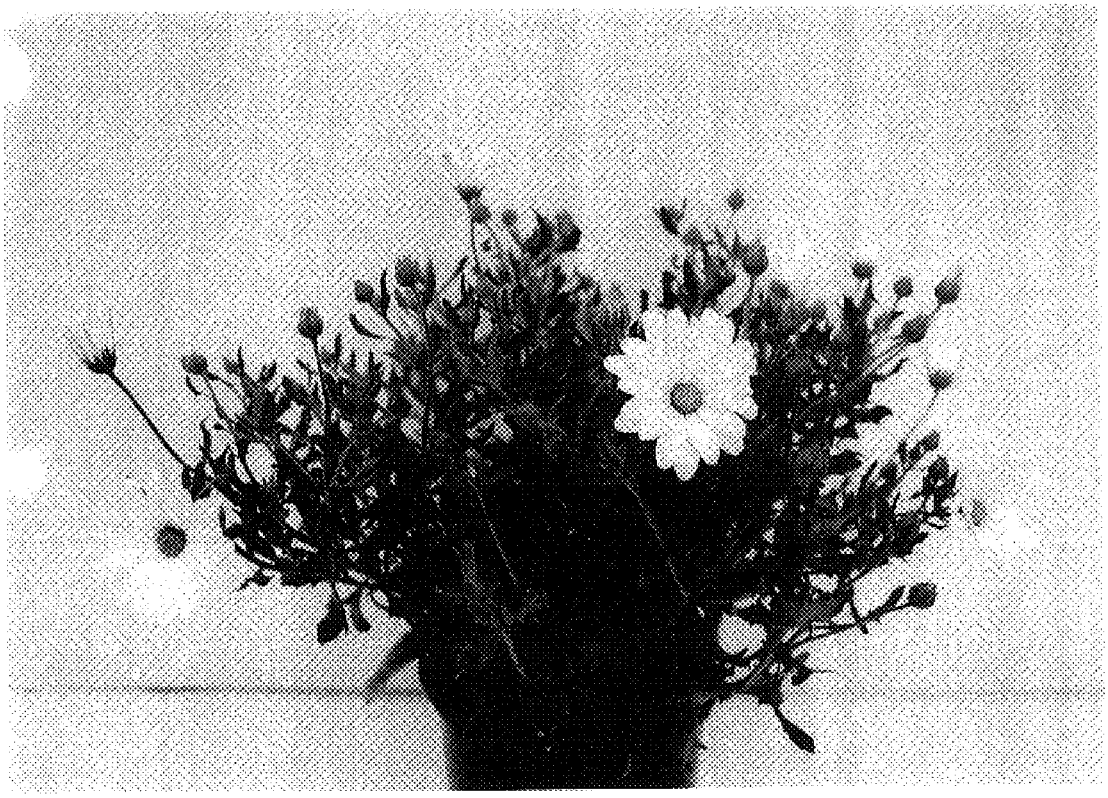

* * * * *